United States Patent
Mienkina et al.

(10) Patent No.: US 11,911,214 B2
(45) Date of Patent: Feb. 27, 2024

(54) SYSTEM AND METHODS FOR AT HOME ULTRASOUND IMAGING

(71) Applicant: GE Precision Healthcare LLC, Milwaukee, WI (US)

(72) Inventors: Martin Paul Mienkina, Neumarkt am Wallersee (AT); Fiona Schwab, Mauerkirchen (AT)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 59 days.

(21) Appl. No.: 17/448,501

(22) Filed: Sep. 22, 2021

(65) Prior Publication Data
US 2022/0000449 A1    Jan. 6, 2022

Related U.S. Application Data

(63) Continuation of application No. 16/802,344, filed on Feb. 26, 2020, now abandoned, which is a
(Continued)

(51) Int. Cl.
*A61B 8/00* (2006.01)
*A61B 5/00* (2006.01)
(Continued)

(52) U.S. Cl.
CPC .......... *A61B 8/4427* (2013.01); *A61B 5/4848* (2013.01); *A61B 8/4254* (2013.01);
(Continued)

(58) Field of Classification Search
CPC ... A61B 5/4848; A61B 8/0858; A61B 8/4254; A61B 8/4427; A61B 8/4444;
(Continued)

(56) References Cited

U.S. PATENT DOCUMENTS 6,390,982 B1    5/2002    Bova et al.
8,777,855 B2    7/2014    Hyun
(Continued)

OTHER PUBLICATIONS

Gerris et al. (Self-operated endovaginal telemonitoring versus traditional monitoring of ovarian stimulation in assisted reproduction: a prospective RCT, Human Reproduction, vol. 0, No. 0 pp. 1-7, 2014; http://fertihome.com/careProviders.php) (Year: 2014).*
(Continued)

*Primary Examiner* — Yi-Shan Yang
*Assistant Examiner* — Alexei Bykhovski
(74) *Attorney, Agent, or Firm* — McCoy Russell LLP (57) ABSTRACT

Various methods and systems are provided for a guided at-home ultrasound imaging session. In one example, a system for ultrasonically scanning a tissue sample includes a hand-held ultrasound probe including a transducer array of transducer elements, a probe position tracking device including one or more position sensors coupled to the ultrasound probe, and a controller. The controller is configured to, during an imaging session, determine a position of the ultrasound probe relative to a target position based on position data collected by the probe position tracking device, and responsive to an indication that the ultrasound probe is at the target position, acquire image data with the transducer array.

20 Claims, 7 Drawing Sheets

Related U.S. Application Data continuation of application No. 15/611,702, filed on Jun. 1, 2017, now abandoned.

(51) Int. Cl.
*G16H 40/63* (2018.01)
*A61B 8/08* (2006.01)

(52) U.S. Cl.
CPC ............ *G16H 40/63* (2018.01); *A61B 8/0858* (2013.01); *A61B 8/4444* (2013.01); *A61B 8/5223* (2013.01); *A61B 8/565* (2013.01); *A61B 8/582* (2013.01)

(58) Field of Classification Search
CPC ....... A61B 8/5223; A61B 8/565; A61B 8/582; G16H 40/63
See application file for complete search history.

(56) References Cited

U.S. PATENT DOCUMENTS

| | | |
|---|---|---|
| 2014/0257104 A1 | 9/2014 | Dunbar et al. |
| 2015/0094585 A1* | 4/2015 | Ter-Ovanesyan .... A61B 8/4444 600/443 |
| 2016/0022308 A1 | 1/2016 | Rohling |
| 2016/0081663 A1* | 3/2016 | Chen ...................... G16H 50/30 600/407 |
| 2016/0119529 A1 | 4/2016 | Stolka et al. |
| 2017/0086797 A1 | 3/2017 | Halmann et al. |
| 2017/0105701 A1* | 4/2017 | Pelissier ................ A61B 8/565 |
| 2017/0143303 A1 | 5/2017 | Chen et al. |
| 2017/0258454 A1 | 9/2017 | Lerch et al. |
| 2018/0085090 A1 | 3/2018 | Park et al. |
| 2018/0129782 A1 | 5/2018 | Himsl et al. |
| 2018/0206819 A1 | 7/2018 | Saarinen et al. |
| 2018/0247023 A1* | 8/2018 | Divine .................... G06T 11/60 |

OTHER PUBLICATIONS

Gerris, J. et al., "Self-operated endovaginal telemonitoring versus traditional monitoring of ovarian stimulation in assisted reproduction: a prospective RCT," Human Reproduction, vol. 0, No. 0, Jul. 3, 2014, 7 pages.

"Make Sonogram," YouTube Website, Available Online at www.youtube.com/watch?v=m7Yjgt21KRA, May 2, 2015, 3 pages.

"Make your own sonograms during IVF treatments," Sonaura Website, Available Online at http://fertihome.com/patient.php, Available as Early as Mar. 31, 2016, 4 pages.

* cited by examiner

SYSTEM AND METHODS FOR AT HOME ULTRASOUND IMAGING

CROSS-REFERENCE TO RELATED APPLICATION

The present application is a continuation of U.S. patent application Ser. No. 16/802,344, entitled "SYSTEM AND METHODS FOR AT HOME ULTRASOUND IMAGING" and filed on Feb. 26, 2020. U.S. patent application Ser. No. 16/802,344 is a continuation of U.S. patent application Ser. No. 15/611,702, entitled "SYSTEMS AND METHODS FOR AT-HOME ULTRASOUND IMAGING" and filed Jun. 1, 2017. The entire contents of each of the above-referenced applications are hereby incorporated by reference for all purposes.

FIELD

Embodiments of the subject matter disclosed herein relate to medical imaging and the facilitation of ultrasonic tissue scanning.

BACKGROUND

Certain medical procedures, such as in vitro fertilization, may include multiple, frequent medical imaging sessions in order to monitor the progress of the procedure. These frequent medical imaging sessions may place a burden on the patient.

BRIEF DESCRIPTION

In one embodiment, a system for ultrasonically scanning a tissue sample includes a hand-held ultrasound probe comprising a transducer array of transducer elements, a probe position tracking device including one or more position sensors coupled to the ultrasound probe, and a controller. The controller is configured to, during an imaging session, determine a position of the ultrasound probe relative to a target position based on position sensor data collected by the one or more position sensors during an imaging session, and responsive to an indication that the ultrasound probe is at the target position, acquire image data with the transducer array.

In this way, the position sensor data may be used to identify the current position of the probe relative to a target position. In one example, the target position of the probe may be a position at which the probe can acquire image data in a target scan plane. Further, in some examples, if the probe is not currently positioned at the target position, feedback may be provided to a user to move the probe to the target position, and then image data may be acquired. This configuration may assist non-clinical users in performing at-home ultrasound imaging, thus reducing the number of in-clinic medical imaging sessions.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 3:
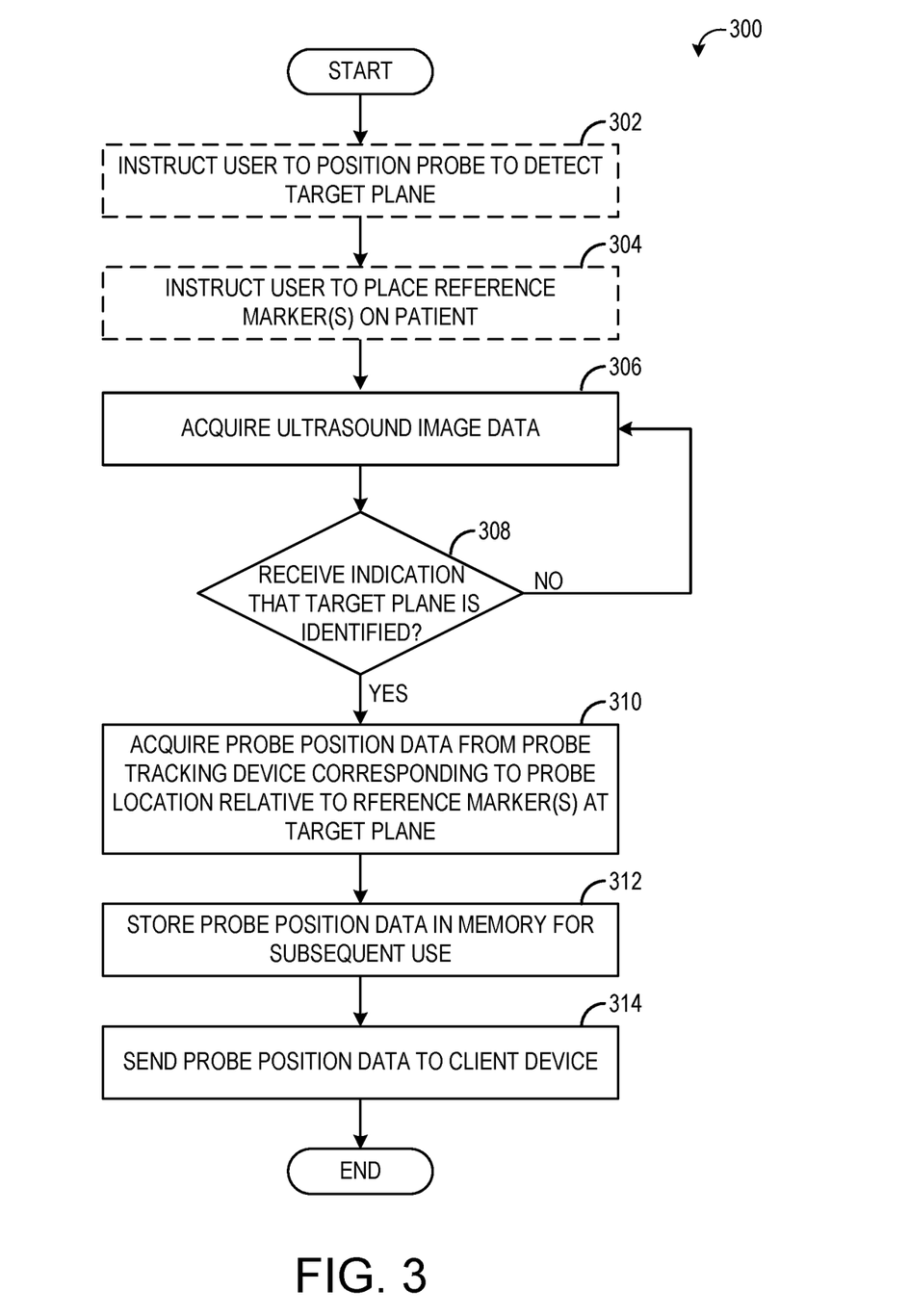
FIG. 3 illustrates a method for identifying a target scan plane according to an embodiment of the invention.
Figure 4:
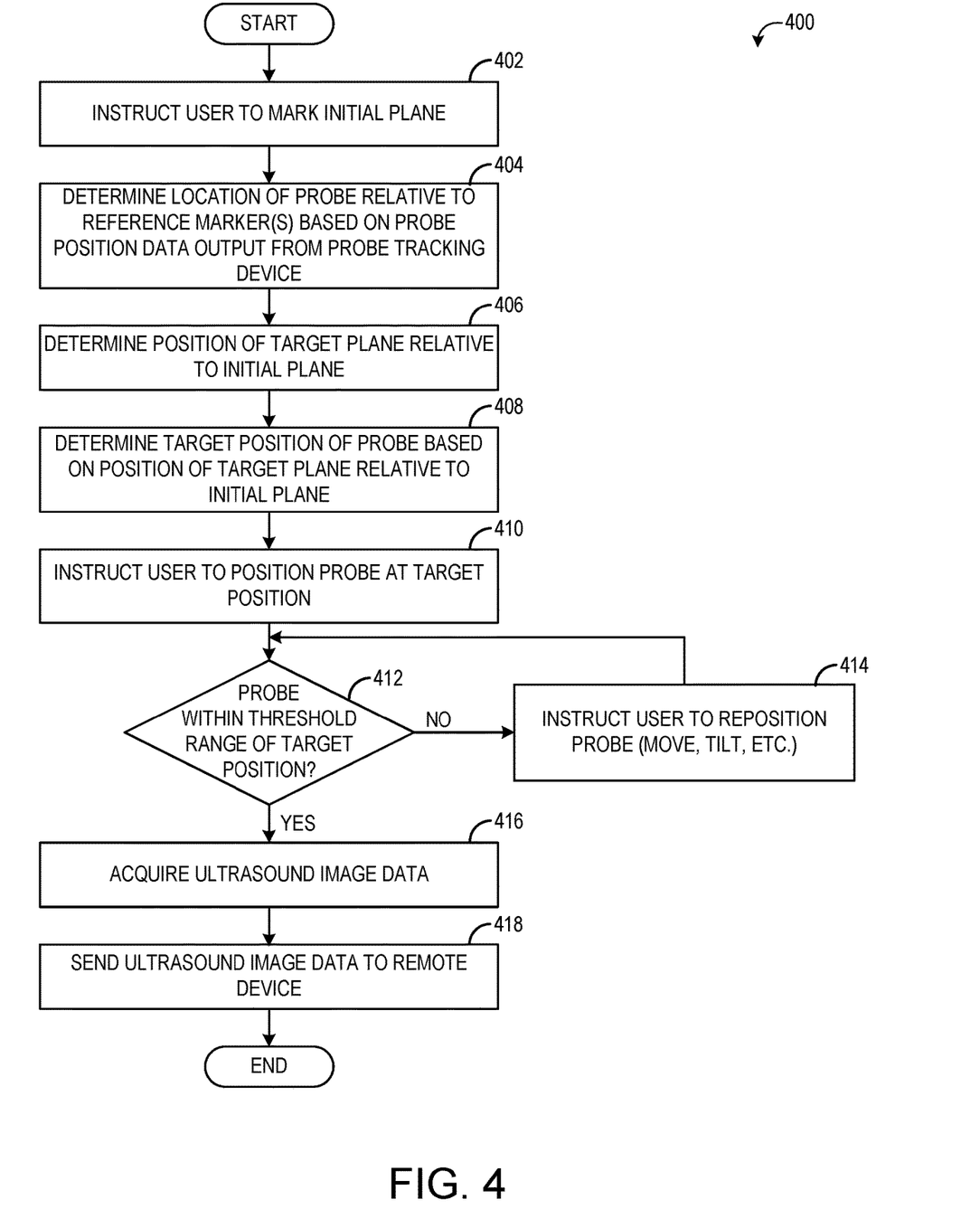
FIG. 4 illustrates a method for at-home ultrasound imaging according to an embodiment of the invention.
Figure 5:
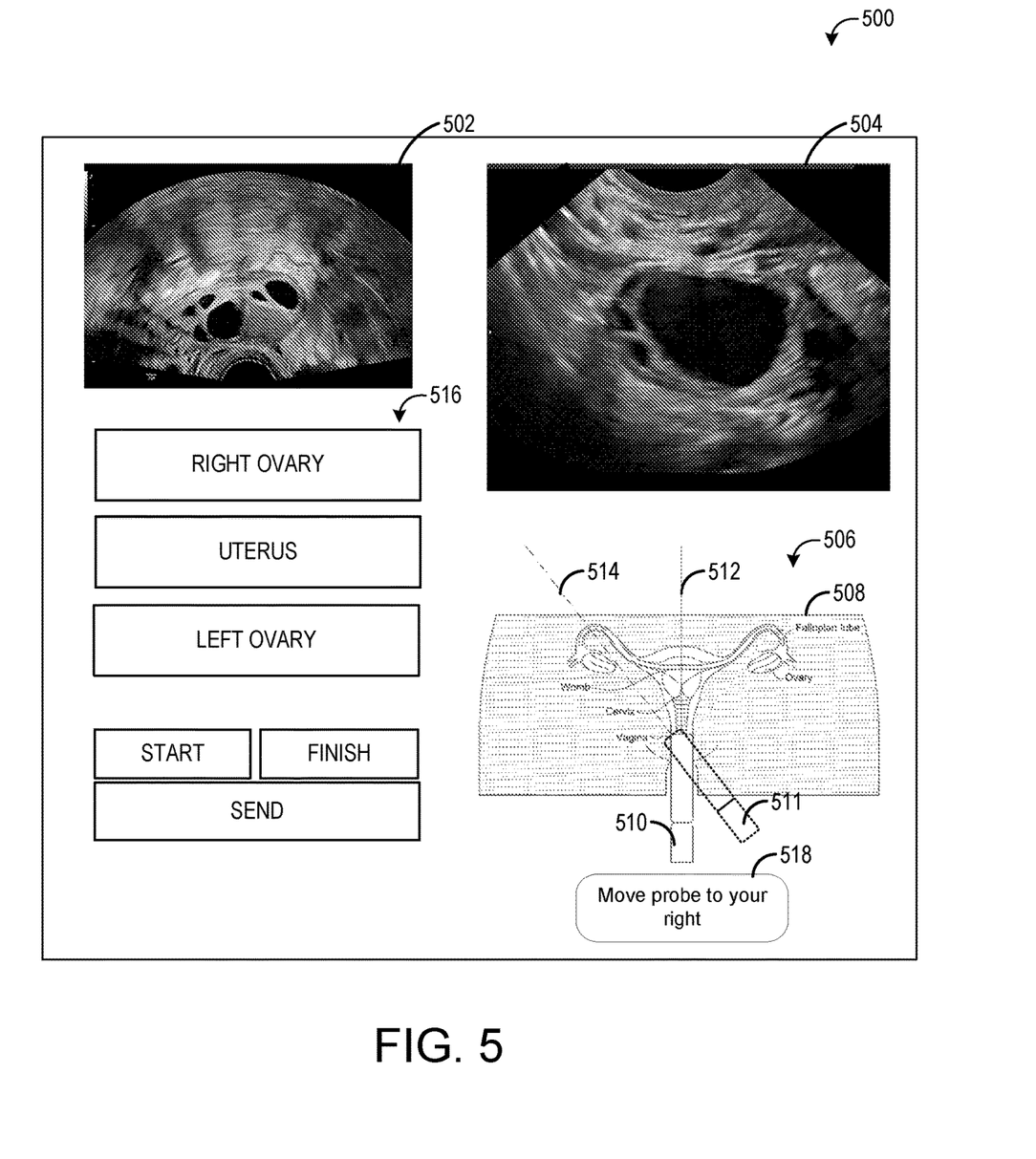
FIGS. 5 and 6 illustrate example user interfaces that may be displayed to an operator during at-home ultrasound imaging according to an embodiment of the invention.
Figure 6:
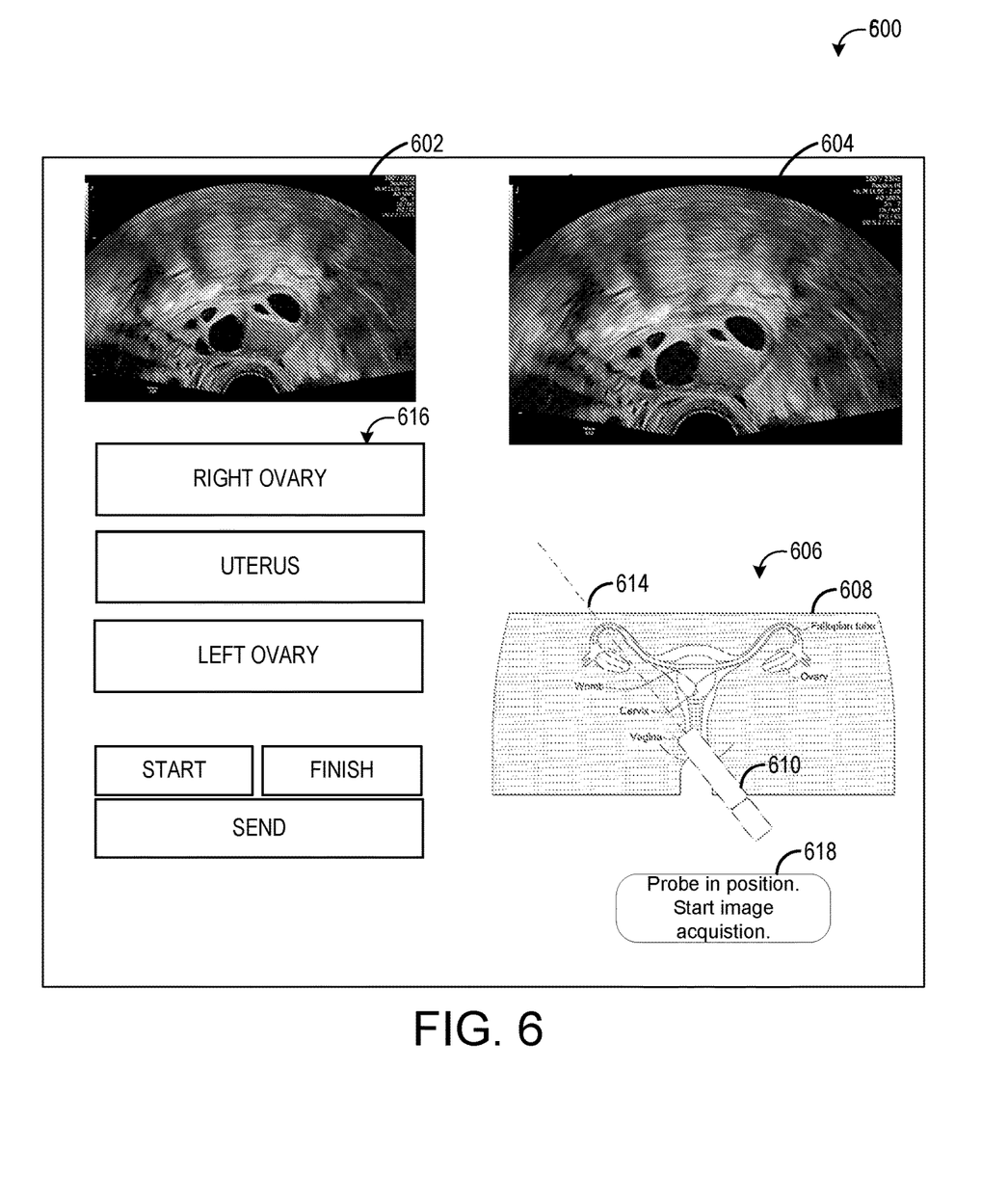
Figure 7:
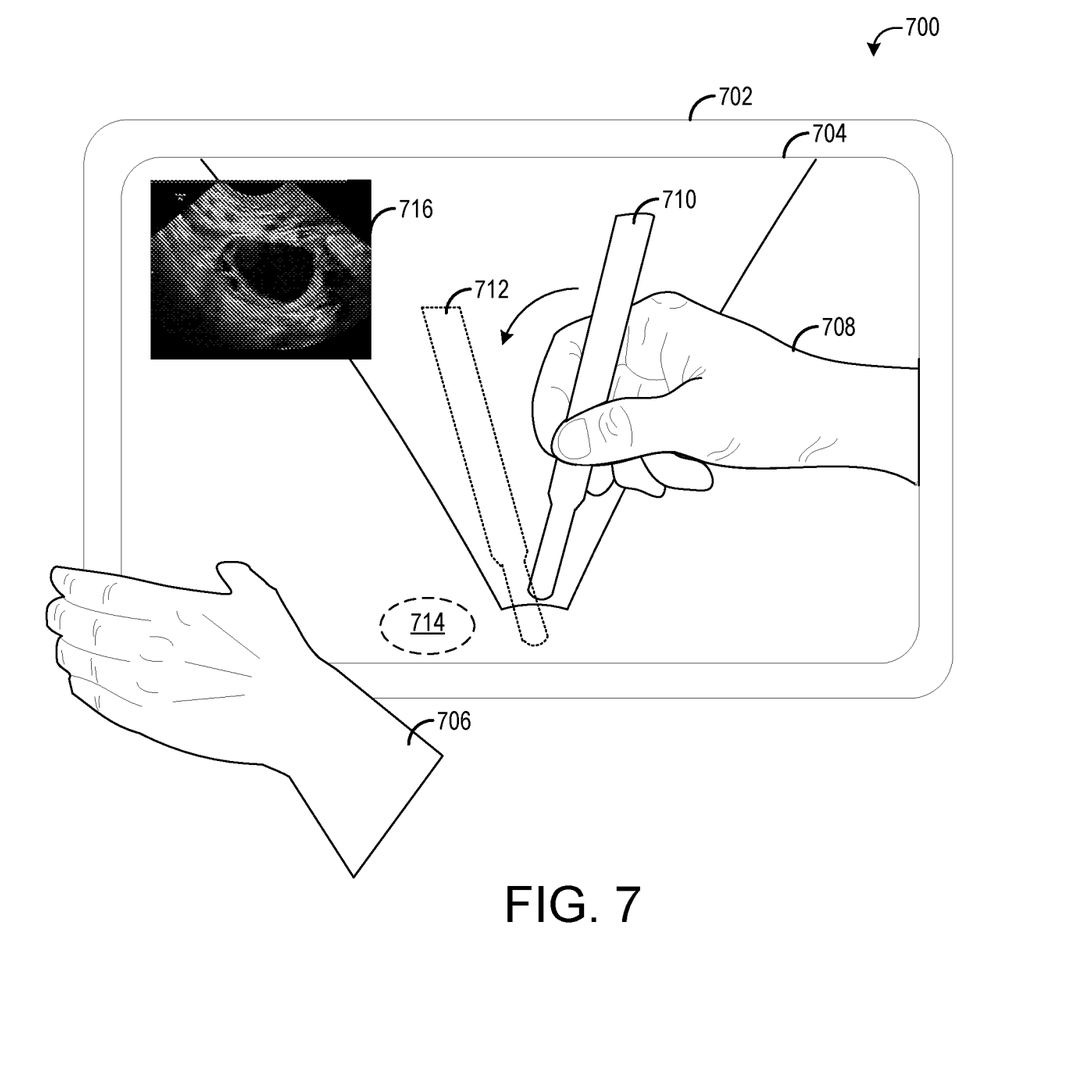
FIG. 7 illustrates an example augmented reality user interface that may be displayed to an operator during at-home ultrasound imaging according to an embodiment of the invention.

The following description relates to various embodiments of an at-home ultrasound system, which may be used during in vitro fertilization (IVF) monitoring. The at-home ultrasound system may include a transvaginal (TV) ultrasound probe, such as the probe illustrated in FIG. 1. In one example, the TV probe may include an ultrasound transducer and a position tracking system that may include one or more position sensors to track the location of the probe, such as the sensors depicted in FIG. 2. The probe may be used to provide semi-automated at-home ultrasound imaging. For example, the sensor information may be used to instruct an operator to position the probe at one or more target locations during the at-home ultrasound imaging. The image information acquired during the imaging may be used to construct a three-dimensional volume from which images may be generated and sent to a remote computing device (e.g., accessible by a clinician) for evaluation. Example methods for performing semi-automated at-home ultrasound imaging using an ultrasound probe are illustrated in FIGS. 3 and 4. Example user interfaces that may be displayed to an operator during a semi-automated at-home IVF monitoring are illustrated in FIGS. 5-7.

In vitro fertilization is an assisted reproductive technology that involves hormonal treatment given to women to trigger their ovaries to produce multiple oocytes. During this treatment, multiple ultrasounds are performed to view the ovaries over a period of time and the acquired ultrasound images may be assessed to determine if the hormonal treatment is working and that the follicles are maturing optimally, and further to identify an optimal time for harvesting of the oocytes. In a typical IVF treatment protocol, a patient may undergo five to six ultrasound imaging sessions over a two-week period. This high frequency of ultrasound imaging sessions may be intrusive and burdensome for the patient, particularly if the patient lives a long distance from a clinic that can perform the ultrasound imaging.

Thus, according to embodiments disclosed herein, frequent monitoring of a medical procedure via ultrasound imaging, such as IVF hormonal treatment monitoring, may be performed by the patient with an at-home ultrasound system. Using the at-home ultrasound system, the patient may perform the ultrasound imaging at home and then send acquired images to a clinician for evaluation. In order to assist the patient with achieving accurate positioning of the ultrasound probe, and thus consistent and accurate image acquisition of the tissue of interest, the ultrasound probe may be equipped with a position tracking system that can determine the current position of the probe relative to a reference marker placed on the patient during an initial, in-clinic ultrasound exam. Also during the initial, in-clinic ultrasound exam, a clinician may identify one or more target scan planes for image acquisition, and the position of the ultrasound probe (relative to the reference marker) for image acquisition at each target scan plane may be stored and sent to a client computing device of the at-home ultrasound system. Then, when the patient performs ultrasound imaging at home, the patient may be guided to adjust the position of the ultrasound probe until the probe is positioned at a target position to acquire images in the one or more target scan planes. Once the probe is at the target position, image acquisition may proceed. Generated images may then be sent to a remote device accessible by the clinician for evaluation.

Although several examples herein are presented in the particular context of human uterus/ovary ultrasound, it is to be appreciated that the present teachings are broadly applicable for facilitating ultrasonic scanning of any human or animal body part (e.g., abdomen, legs, feet, arms, neck, etc.). Moreover, although several examples herein are presented in the particular context of manual/hand-held scanning (e.g., in which the ultrasound probe is moved by an operator), it is to be appreciated that one or more aspects of the present teachings can be advantageously applied in a mechanized scanning context (e.g., a robot arm or other automated or semi-automated mechanism).

Figure 1:
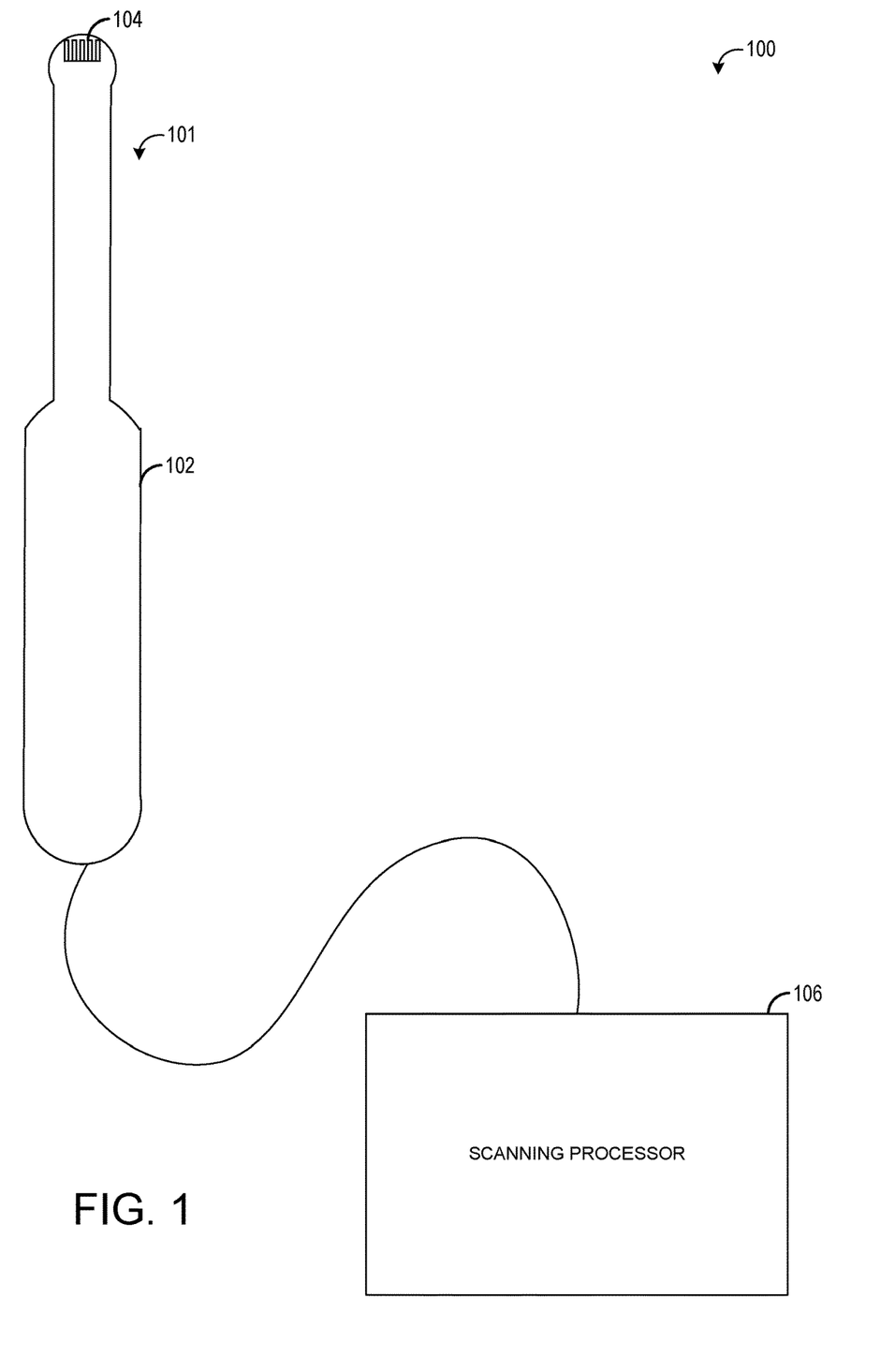
FIG. 1 shows an example of an ultrasound imaging system according to an embodiment of the invention.

FIG. 1 illustrates an example hand-held ultrasound system 100 that is configured for performing transvaginal ultrasounds. The hand-held ultrasound system 100 includes a transvaginal (TV) probe 101 that includes a housing 102 in which an ultrasound transducer array 104 is positioned. The transducer array is positioned at the scan head and is inserted into the tissue to be scanned, thus producing a sharper image relative to externally-applied probes because of the proximity of the transducer array to the tissue lining. The probe 101 may comprise a position tracking device including one or more position sensors (shown in FIG. 2) to allow position and orientation sensing for the transducer. Suitable position sensors (e.g., gyroscopic, magnetic, optical, radio frequency (RF)) may be used.

A fully-functional ultrasound engine for driving an ultrasound transducer and generating volumetric trans-vaginal ultrasound data from the scans in conjunction with the associated position and orientation information may be coupled to the probe, for example the ultrasound engine may include a processor and memory and/or be implemented with a processor and memory. The ultrasound engine may be included as part of a scanning processor 106 coupled to the probe. The volumetric scan data can be transferred to another computer system for further processing using any of a variety of data transfer methods known in the art. A general purpose computer, which can be implemented on the same computer as the ultrasound engine, is also provided for general user interfacing and system control. The ultrasound system may be a self-contained stand-alone unit that may be moved from room to room, such as a cart-based system, a hand-carried system or other portable system. Further the ultrasound system of FIG. 1 may be remotely controlled, configured, and/or monitored by a remote station connected across a network.

Figure 2:
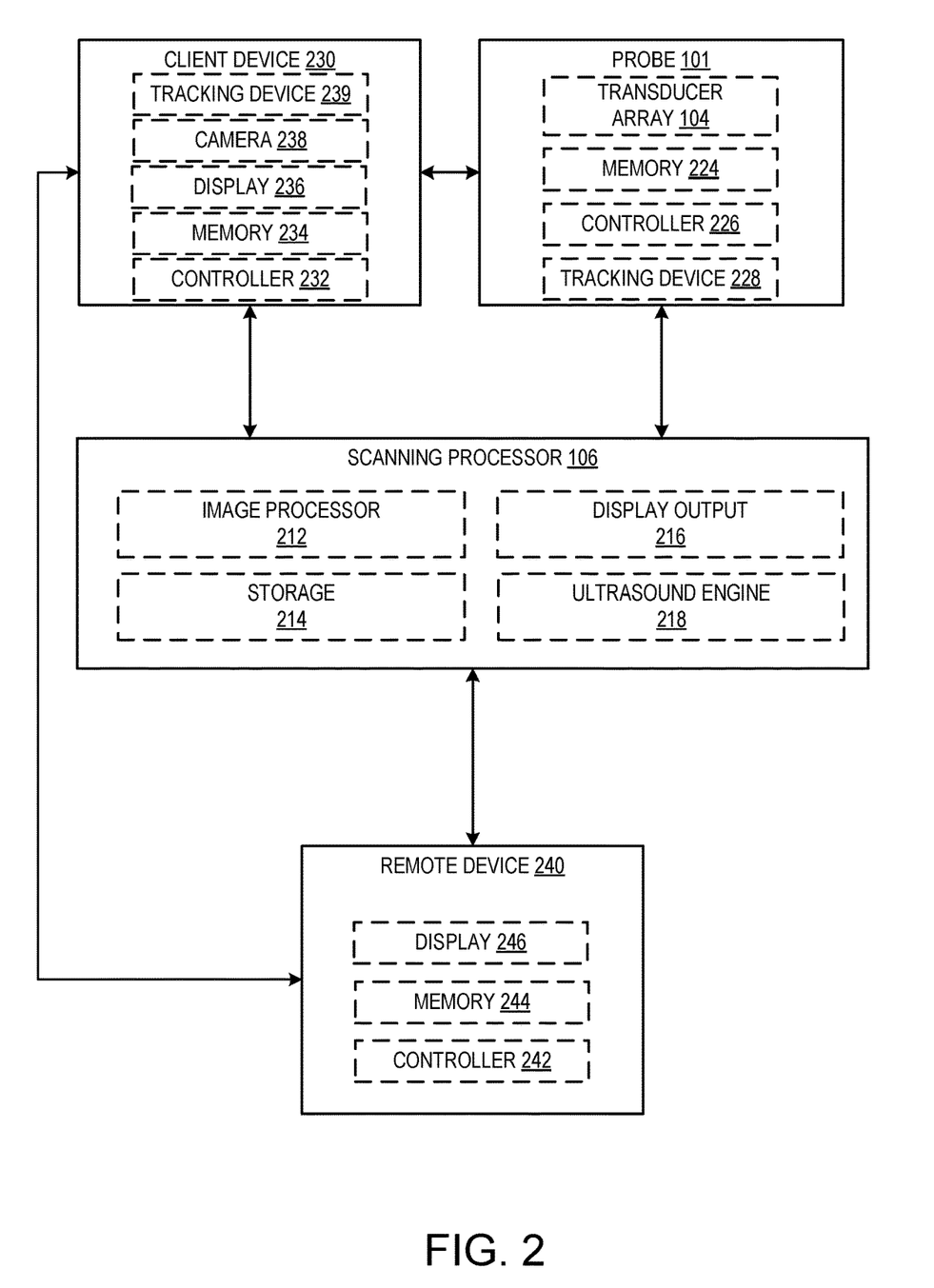
FIG. 2 shows an example schematic of various system components of an ultrasound imaging system according to an embodiment of the invention.

FIG. 2 is a block diagram 200 schematically illustrating various system components of an ultrasound imaging system, including the probe 101, the scanning processor 106, a client device 230, and a remote device 240. In some embodiments, the scanning processor may be further coupled to a remote department information system, hospital information system, and/or to an internal or external network to allow operators at different locations to supply commands and parameters and/or gain access to image data (as explained in more detail below, remote device 240 is one non-limiting example of one such remote system to which the scanning processor may be coupled).

Referring first to the probe 101, the probe 101 comprises the transducer array 104. As explained above with respect to FIG. 1, the transducer array may be positioned within the housing, and the housing and transducer array may be configured to be moved manually by an operator during an ultrasound exam. The transducer array may include an array of transducer elements, such as piezoelectric elements, that convert electrical energy into ultrasound waves and then detect the reflected ultrasound waves.

The probe 101 may further include a memory 224. Memory 224 may be a non-transitory memory configured to store various parameters of the transducer array 104, such as transducer position information obtained from a position tracking device 228 of the probe, transducer usage data (e.g., number of scans performed, total amount of time spent scanning, etc.), as well as specification data of the transducer (e.g., number of transducer array elements, array geometry, etc.) and/or identifying information of the probe 101, such as a serial number of the probe. Memory 224 may include removable and/or permanent devices, and may include optical memory, semiconductor memory, and/or magnetic memory, among others. Memory 224 may include volatile, nonvolatile, dynamic, static, read/write, read-only, random-access, sequential-access, and/or additional memory. In an example, memory 224 may include RAM. Additionally or alternatively, memory 224 may include EEPROM.

Memory 224 may store non-transitory instructions executable by a controller or processor, such as controller 226, to carry out one or more methods or routines as described herein below. Controller 226 may receive output from various sensors of the tracking device 228 and trigger actuation of one or more actuators and/or communicate with one or more components in response to the sensor output. In one example, the tracking device 228 may include one or more position sensors, accelerometers, gyroscopes, pressure sensors, strain gauge sensors, and/or temperature sensors. The tracking device 228 may further include a reference marker detector configured to detect a reference marker positioned on a patient undergoing ultrasound scanning. The reference marker detector may be configured to detect a magnetic reference marker, optical reference marker, or other suitable reference marker positioned internally or externally of the patient. Prior to and/or during image acquisition, the position of the probe (in six degrees of freedom, including translation across and rotation about three perpendicular axes) relative to the reference marker may be determined from the output of the position sensor(s) of the tracking device 228 and stored in memory 224 and/or sent to the scanning processor 106. The output from the sensors may be used to provide feedback to an operator of the probe 101 (via a displayed user interface of scanning processor 106, client device 230, and/or another device). For example, the operator may be instructed to reposition the probe prior to image acquisition, if the probe is not located at a predetermined position. In another example, the operator may be instructed to adjust an angle, depth, and/or location of probe during scanning.

Probe 101 may be in communication with scanning processor 106 to send raw scanned data to an image processor 212, for example. Additionally, data stored in memory 224 and/or output from tracking device 228 may be sent to scanning processor 106 in some examples. Further, various actions of the probe 101 (e.g., activation of the transducer elements) may be initiated in response to signals from the scanning processor 106. Probe 101 may optionally communicate with a display of the scanning processor and/or display 236 of the client device, in order to notify a user to reposition the probe 101, as explained above, or to receive information from a user, for example.

Turning now to scanning processor 106, it includes an image processor 212, storage 214, display output 216 configured to send information for display on a display device of the scanning processor 106 and/or another display device (such as a display of remote device 240), and ultrasound engine 218. Ultrasound engine 218 may drive activation of the transducer elements of the transducer array 104. Further, ultrasound engine 218 may receive raw image data (e.g., ultrasound echoes) from the probe 101. The raw image data may be sent to image processor 212 and/or to a remote processor (via a network, for example) and processed to form a displayable image of the tissue sample which may be sent to a coupled display device via the display output 216. It is to be understood that the image processor 212 may be included with the ultrasound engine 218 in some embodiments.

Information may be communicated from the ultrasound engine 218 and/or image processor 212 to a user of the ultrasound probe system via the display output 216 of the scanning processor 106. In one example, the user may include an ultrasound technician, nurse, or physician such as a radiologist. For example, after acquiring imaging data (e.g. ultrasound imaging data) in real time, an image may be generated from the data and displayed on a display device (of the scanning processor 106 or an operatively coupled device) via the display output 216. In another example, information relating to parameters of the scan, such as the progress of the scan, may be sent to the display via the display output 216. In another example, the display output 216 may output a user interface configured to display images or other information to a user. Further, the user interface may be configured to receive input from a user and send the input to the scanning processor 106. User input may be via a touch screen of a display in one example. However, other types of user input mechanisms are possible, such as a mouse, keyboard, etc.

Scanning processor 106 may further include storage 214. Similar to memory 224 of the probe, storage 214 may include removable and/or permanent devices, and may include optical memory, semiconductor memory, and/or magnetic memory, among others. Storage 214 may include volatile, nonvolatile, dynamic, static, read/write, read-only, random-access, sequential-access, and/or additional memory. Storage 214 may store non-transitory instructions executable by a controller or processor, such as ultrasound engine 218 or image processor 212, to carry out one or more methods or routines as described herein below. Storage 214 may store position information of the ultrasound probe as communicated via the tracking device 228. Storage 214 may store raw image data received from the ultrasound probe, processed image data received from image processor 212 or a remote processor, and/or additional information.

The scanning processor 106 and/or probe 101 may be communicatively coupled to a client device 230. The client device 230 may include a suitable computing device, such as a laptop, tablet, or mobile device. The client device 230 may include a controller 232, memory 234, display 236, and camera 238. The controller 232 may include an image processor and ultrasound engine, similar to the image processor and ultrasound engine of the scanning processor 106. In this way, the client device 230 may drive actuation of the elements of the transducer array 104 of the probe 101, receive raw image data from the probe 101, and/or process the raw image data into one or more images. The controller 232 may further execute instructions stored in memory 234 in order to carry out one or more of the methods described herein.

Memory 234 may include volatile, nonvolatile, dynamic, static, read/write, read-only, random-access, sequential-access, and/or additional memory. Memory 234 may store non-transitory instructions executable by a controller or processor, such as controller 232, to carry out one or more methods or routines as described herein below. Memory 234 may store position information of the ultrasound probe as communicated via the tracking device 228 of the probe. Memory 234 may store raw image data received from the ultrasound probe, processed image data received from the image processor, and/or additional information.

The display 236 may display suitable information, such as one or more user interfaces, images, etc. The display 236 may display content sent from controller 232 or other suitable processor. The camera 238 may include both forward-facing and rear-facing image sensors each configured to acquire visible light and/or light-based depth images. Visible light images and/or light-based depth images may be displayed on display 236 in the form of still images and/or videos. In some examples, data from the forward- and/or rear-facing image sensors may also be used to determine direction/location and orientation data (e.g. from imaging environmental features) that enables position/motion tracking of the client device 230 in the real-world environment.

Client device 230 may further include a tracking device 239. Tracking device 239 may be configured to provide position and/or orientation data of the client device 230 to the controller 232. In one example, the tracking device may be configured as an inertial movement unit (IMU) including a three-axis or three-degree of freedom (3 DOF) position sensor system. This example position sensor system may, for example, include three gyroscopes to indicate or measure a change in orientation of the client device within 3D space about three orthogonal axes (e.g., roll, pitch, and yaw). The orientation derived from the sensor signals of the IMU may be used to display, via the display 236, one or more augmented reality images with a realistic and stable position and orientation.

In another example, the IMU may be configured as a six-axis or six-degree of freedom (6 DOF) position sensor system. Such a configuration may include three accelerometers and three gyroscopes to indicate or measure a change in location of the client device along three orthogonal spatial axes (e.g., x, y, and z) and a change in device orientation about three orthogonal rotation axes (e.g., yaw, pitch, and roll). In some embodiments, position and orientation data from the image sensors and the IMU may be used in conjunction to determine a position and orientation of the client device.

Client device 230 may be communicatively coupled to a remote device 240. Remote device 240 may include a suitable computing device usable to store and/or display acquired ultrasound images, and may also be communicatively coupled to scanning processor 106. Remote device 240 may be part of a picture archiving and communication system (PACS) that is configured to store patient medical histories, imaging data, test results, diagnosis information, management information, and/or scheduling information, for example. The remote device 240 may comprise a PACS server that includes computer-readable storage media suitable for storing image data for later retrieval and viewing at a PACS workstation, for example. Remote device 240 may include a controller 242, memory 244, and/or display 246. Memory 244 may include volatile, nonvolatile, dynamic, static, read/write, read-only, random-access, sequential-access, and/or additional memory. Memory 244 may store non-transitory instructions executable by a controller or processor, such as controller 242, to carry out one or more methods or routines as described herein below. Memory 244 may store position information of the ultrasound probe as communicated via the tracking device 228 of the probe. Memory 244 may store raw image data received from the ultrasound probe, processed image data received from the image processor, and/or additional information.

Turning now to FIG. 3, a method 300 for identifying a target scan plane during an imaging session prior to an at-home imaging session is illustrated. Method 300 may be executed by a computing device such as client device 230, scanning processor 106, and/or a computing device in communication with the scanning processor 106, such as remote device 240, according to instructions stored in memory thereof, in conjunction with a hand-held ultrasound probe, such as probe 101.

At 302, method 300 optionally includes instructing a user to position the ultrasound probe to detect a target plane. The user may be a clinician, such as a sonographer, and may also be referred to herein as a first operator. Instructing the user may include outputting instructions (e.g., via a display device) that may guide or otherwise instruct the user to adjust the position of the ultrasound probe until the probe is imaging the target plane. The target plane may include a predetermined scan plane of desired tissue to be scanned (e.g., an ovary of a patient).

At 304, method 300 optionally includes providing further instructions to the user to place one or more reference markers on the patient. The reference markers may include markers detectable by a suitable detection system, such as magnetic or optical markers. The instructions may guide the user to place the markers at designated positions in some examples. For example, the one or more reference markers may be placed at or near the target plane, on a designated portion of the patient's anatomy, etc.

At 306, method 300 includes acquiring ultrasound image data of the tissue. The received image data may include ultrasound echoes of ultrasound waves transmitted by the transducer elements of the transducer array of the ultrasound probe. The ultrasound echoes may be sent to an image processor such as image processor 212 to be processed into a real-time image of the tissue that may be displayed via display output 216 of the scanning processor 106. In some examples, the image data may include volumetric ultrasound data.

At 308, method 300 determines if the target plane has been identified. The identification of the target plane may be determined based on user input in one example. For example, the user of the ultrasound probe may press a button, enter input on a touch screen, or provide other suitable user input that indicates the ultrasound probe is currently imaging in the target plane. In another example, the target plane may be identified automatically by the computing device using image recognition trained via machine learning, for example. If it is determined that the target plane was not identified, method 300 reverts back to 306 and continues to acquire ultrasound image data of the tissue.

However, if it is determined that the target plane was identified, method 300 proceeds to 310 to acquire probe position data from a probe position tracking device, such as tracking device 228, which may include one or more probe position sensors. The probe position data may indicate the current probe location and orientation relative to the one or more reference markers at the target plane, and thus the method may also include determining respective positions of each reference marker via the probe position tracking device. At 312, method 300 stores the probe position data of the probe relative to the reference markers at the target plane in the memory of the computing device, for subsequent at-home ultrasound probe use. Method 300 at 314 optionally sends the probe position data to a remotely connected client device. For example, if method 300 is performed by scanning processor 106, remote device 240, or another device permanently located in a clinic/hospital, the probe position data may be sent to a client device such as device 230 of FIG. 2. The probe position data may include probe position information (e.g., in six degrees of freedom) relative to each position of each reference marker, and may further include the target plane scanned by the probe at that probe position, such as right ovary, left ovary, uterus, etc. Method 300 then returns.

Turning now to FIG. 4, a method for at-home ultrasound imaging is illustrated. Method 400 may be executed by a computing device, such as client device 230, according to instructions stored in memory thereof, in conjunction with a hand-held ultrasound probe, such as probe 101 or another similarly configured probe. For example, the probe used during the execution of method 300 described above may be the same probe used in the execution of method 400, or it may be a different, though similarly configured, probe. Likewise, the computing device executing method 400 may be the same computing device that executed method 300, or it may be a different computing device in communication with the computing device that executed method 300.

At 402, method 400 includes instructing a user to position the ultrasound probe and detect an initial plane. The user may be a patient undergoing IVF treatment or another non-clinical user, and may also be referred to herein as a second operator. The user may identify the initial plane via instructions and image data displayed via the user interface of a display associated with the computing device, for example. The displayed image data may include one or more images such as a reference image of the desired target plane and a real-time image generated from image data acquired by the ultrasound probe at the current probe position, for example as shown in FIGS. 5 and 6, described in more detail below. In some examples, the generated images may include position identifying information. The user interface may further include instructions for guiding the user of the probe to mark an initial position of the probe as the initial plane, such as by pressing a button on the probe or other by enter another user input.

At 404, method 400 determines the current location of the probe at the initial plane relative to the location(s) of the reference marker(s) based on probe position data output from the probe tracking device that includes position sensor (s). As explained above, the probe may include one or more position sensors that may output position sensor data usable to determine a current position of the probe and the probe may include a reference marker detector that may output a position of each reference marker. At 406, method 400 determines the position and orientation of the target plane relative to the initial plane. The target plane may be identified in a previous imaging session by a physician or other clinician and the position of the target plane may be stored in memory of the client device executing method 500.

At 408, method 400 determines a target position of the probe based on the position of the target plane relative to the initial plane. The target position of the probe may be a position at which the target plane is imageable by the probe. As explained above, the computing device may obtain the stored probe position data indicating the target position of the probe relative to the reference markers and/or the target plane. The computing device may further compute a distance and/or a clock position for the probe to be moved in order to be positioned at the desired target plane. The computed distance and/or clock position relative to one or more reference marker(s) may then be displayed as instructions on the display for the user, at least in some examples.

Accordingly, at 410, method 400 instructs the operator to position the probe at the target position. For example, a user interface on the display may display instructions guiding the operator to position the ultrasound probe. The computing device may receive output from the position sensor(s) while the operator is positioning the probe, and the computing device may instruct the operator to position the ultrasound probe based on the output from the position sensor(s). For example, the computing device may determine that the probe is positioned two cm to the right of the target position and then output instructions to the user to move the probe two cm to the left.

At 412, method 400 determines if the probe is within a threshold range of the target position. The computing device may receive output from the position sensor(s) after the operator has completed positioning the probe and may determine from the received output if the probe is within a threshold range of the target position. The threshold range may be a suitable range of distances, angles, depths, etc., around the target position, such as within 1 cm or less of the target position (e.g., left, right, up, and down), within 5 degrees of the target position (e.g., of a horizontal, vertical, and/or lateral axis), etc. If the ultrasound probe is not within the threshold range of the target position, method 400 moves to 414 to instruct the operator to reposition (e.g. move, tilt, etc.) the probe. Method 400 then returns to continue assessing if the probe is within the threshold range of the target position.

If the ultrasound probe is within the threshold range of the target position as determined by the position sensor data output, then method 400 proceeds to 416 to acquire ultrasound image data. In some examples, the method may automatically acquire ultrasound image data responsive to the probe within a threshold range of the target position, though it should be appreciated that in other examples, the method may acquire ultrasound image data responsive to manual user input received once the user has positioned the probe within the threshold range. The image data may include ultrasound echoes of ultrasound waves transmitted by the transducer elements of the transducer array of the ultrasound probe. The ultrasound echoes may be sent to an image processor to be processed into a real-time image of the tissue that may be displayed. In some examples, the image data may include volumetric ultrasound data. While method 400 has been described with respect to only acquiring image data at 416 once the probe is within range of the target position, it is to be understood that in some examples, image data may be acquired via the ultrasound probe throughout the execution of method 400. In one example, non-volumetric ultrasound data may be acquired prior to 416 in order to allow the user to visualize the initial plane and then eventually the target plane, and then once the probe is at the target position, volumetric image data acquisition may proceed.

At 418, method 400 proceeds to send the acquired ultrasound image data to a remote device, such as remote device 240. In some examples, the ultrasound image data may include positional information corresponding to the precise tissue anatomy that indicates the plane of each image and the direction/positon relative to the desired target plane and/or reference marker(s). By doing so, future ultrasound exams may be conducted and images of the same location taken over each exam may be compared, to facilitate accurate compare-to-prior workflow exams. Method 400 then returns.

Thus, method 400 of FIG. 4 facilitates an at-home ultrasound imaging session by obtaining probe position data indicative of a position of the ultrasound probe relative to one or more reference markers, and using the probe position data to guide a (non-clinically trained) user to position the ultrasound probe at a target position. The target position of the ultrasound probe may be a position at which the probe is able to image at a designated/target scan plane. The target position of the probe at the target scan plane may be specified during a prior imaging session conducted by a clinician, for example, and stored in memory of the computing device coupled to (and configured to drive) the ultrasound probe. Once the ultrasound probe is in the target position (or within a threshold range of the target position), volumetric ultrasound image data may be acquired by the ultrasound probe. The image data may be sent to a remote computing device accessible by a clinician, where the image data may be evaluated by the clinician to monitor the progress of medical procedure (e.g., to measure follicle size and in turn determine the optimal time for oocyte retrieval during IVF).

In some examples, the computing device may be configured to automatically monitor the progress of the medical procedure in addition to or alternative to sending the image data to the clinician for evaluation. As explained above, the at-home ultrasound imaging session may be part of an on-going medical procedure such as IVF follicle monitoring. The computing device may be configured to perform image recognition on the acquired ultrasound image data to automatically identify a stage of the medical procedure. For example, the computing device may compare the acquired image data with the reference image of the target plane taken during the prior imaging session, pixel by pixel or voxel by voxel, to determine changes in the anatomy of the tissue scanned. In another example, the computing device may be configured to detect one or more anatomical features and determine changes in the acquired real-time image(s) compared to the reference image at the target plane taken at a previous time. In some examples, the use of convoluted neural networks may aid and/or improve feature detection and identification, as permitted by algorithm performance and system features. The position sensor output information may be used to aid or enhance this registration, for example by aligning image data sets or by defining a region of interest where the anatomical feature is likely to be located (in order to expedite the detection of the anatomical feature, for example). In one example, the acquired ultrasound image at the target plane may be compared with another acquired ultrasound image taken via the same method certain time duration prior (e.g., a week prior) to determine changes in the tissue anatomy.

Further, while method 400 described above included the user marking an initial scan plane, determining a position of the target plane relative to the initial plane, and determining a target position of the probe relative to the initial plane and target plane, in some examples the marking of the initial scan plane may be dispensed with, or may not be used during the probe position adjustment. For example, the computing device may begin tracking the position of the probe responsive to user input, responsive to the ultrasound probe being powered on, or responsive to the computing system automatically detecting that the probe is being used to image the anatomy of interest (e.g., responsive to the probe being inserted into the patient). Once the tracking of the probe has commenced, the target position of the probe relative to the one or more reference markers may be obtained from memory of the computing device, where the target position indicates the position of the probe relative to the one or more reference markers at the target scan plane. Suitable tracking mechanisms (e.g., dead reckoning) may be used to track the position of the probe as the user manipulates the probe and to determine instructions to be output to the user to guide the user to adjust the position of the probe until the probe reaches the target position. Once the probe is at the target position, the user may be instructed to enter an input to initiate image acquisition or the computing device may automatically initiate image acquisition once it determines the probe is at the target position.

FIG. 5 shows an example user interface 500 that may be output (e.g. by controller 232 for display via a display device, such as display 236) during the execution of method 400 (e.g., during an-home ultrasound exam). User interface 500 may include a reference image 502 (e.g., an image of the target scan plane acquired during a prior imaging session), a real time image 504, a navigation tool 506, and a plurality of control buttons 516. The navigation tool 506 may include a depiction 508 of the anatomy being imaged, a depiction 510 of the probe, a depiction 511 of a target probe position, a current scan plane marker 512, and a target scan plane marker 514. The user interface may further include instructions 518 to guide the user to adjust the probe. The control buttons may include buttons indicating the target anatomy (e.g., right ovary, uterus, and left ovary), a start button, a finish button, and a send button.

At the beginning of the ultrasound imaging session, the user may indicate which anatomy is to be imaged by selecting one of the target anatomy buttons (e.g., by touching the right ovary button). This may notify the computing device which target scan plane and hence which target probe position is to be used to guide the user prior to image acquisition.

As shown by the user interface 500, the probe is not positioned at the target position and hence the probe is not imaging at the target scan plane. For example, the depiction 510 of the probe shows that the probe is aligned with the current scan plane marker 512 and not with the target probe position or the target scan plane marker 514. Thus, user interface 500 prompts the user to move the probe to the indicated target plane and target probe position after computing the initial plane location relative to the target plane and/or reference marker location. The user interface may include instructions that are given in real-time, e.g., as the operator moves and positions the probe, the depicted location of the probe may change to reflect the updated location of the probe. The instructions 518 may be displayed to include text that guides the operator to the target plane, e.g., "move the probe 1 cm to your right." In some examples, the depiction 508 of the anatomy, the depiction 510 of the probe, and depiction 511 of the target probe position may be illustrated as mirror images of the user, where the right side of the user is depicted on the left side of the image and vice versa, while in other examples, the depiction 508 of the anatomy, the depiction 510 of the probe, and depiction 511 of the target probe position may be illustrated as non-mirror images where the right side of the user is depicted on the right side of the image and vice versa. The instructions 518 may take into account the perspective of the user relative to the display and depictions on the display and may define that the user is to move the probe relative to the user (as illustrated), relative to a portion of the anatomy, or other suitable instruction.

FIG. 6 shows another example user interface 600 that may be output (e.g. for display via a display device, such as display 236) during the execution of method 400 (e.g., during an-home ultrasound exam). User interface 600 may include a reference image 602 (e.g., an image of the target scan plane acquired during a prior imaging session), a real time image 604, a navigation tool 606, and a plurality of control buttons 616. The navigation tool 606 may include a depiction 608 of the anatomy being imaged, a depiction 610 of the probe, and a target scan plane marker 614. The user interface may further include instructions 618 to the user. The control buttons may include buttons indicating the target anatomy (e.g., right ovary, uterus, and left ovary), a start button, a finish button, and a send button, as explained above with respect to FIG. 5.

As illustrated by user interface 600, the user has moved the probe to the target position. As such, the probe is aligned with the target scan plane, and the real time image is imaging the same scan plane as the reference image (while FIG. 6 shows the reference image being identical to the real time image, in some examples the real time image may have a different appearance than the reference image, due to changes in the oocyte/follicle development, for example). The instructions 618 are notifying the user that the probe is in the target position and that image acquisition can begin. The user may initiate image acquisition by touching the start button, at least in one example. In other examples, the computing device may automatically initiate image acquisition once it determines the probe is in the target position.

When image acquisition begins, the start button may be highlighted or have another visual indicator that indicates acquisition is occurring. When image acquisition is complete, the finish button may be highlighted and/or the send button may be highlighted, to notify the user that the image data is ready to send to the remote device. Additionally, the button of the target anatomy that was just imaged (e.g., the right ovary) may be highlighted to notify the user that the image acquisition for that anatomy is complete.

FIG. 7 illustrates an example of an augmented reality user interface 700 that may be displayed during an at-home ultrasound imaging session. The augmented reality user interface 700 may be displayed on a display 704 of a client device 702, herein in the form of a tablet. Client device 702 is a non-limiting example of client device 230 of FIG. 2.

Client device 702 is being held by a user, as shown by left hand 706 of the user. Client device 702 is collecting visible light images of the user via the camera of client device 702 and displaying the visible light images in real-time on display 704. Accordingly, a right hand 708 of the user is depicted in the visible light images displayed on display 704. The user is holding an ultrasound probe (such as probe 101), and thus an ultrasound probe 710 is also depicted in the visible light images displayed on display 704. The client device 702 may be configured to generate a 2D or 3D model of the physical environment surrounding the client device 702 based on visible light and/or light-based depth information collected by the camera of the client device 702 as well as position and orientation information collected by the tracking device of the client device 702. In some examples, the user may be instructed to move the client device 702 in order to allow the client device 702 to obtain sufficient image, position, and orientation information to generate the 2D or 3D model of the physical environment.

In some examples, the client device 702 may include a reference marker 714 of the user in the generated 2D or 3D model. The reference marker 714 may be a magnetic, optical, or other suitable reference marker that may be visible in the visible light images displayed on display 704, although in some examples the reference marker 714 may not be visible (e.g., the reference marker may be positioned within the user).

As explained above, a target probe position may be determined during a prior imaging session and saved in memory of the client device 702. The target probe position may include a position and orientation of the probe relative to the reference marker 714 at which the target scan plane may be imaged. The client device 702 may determine the current position of the ultrasound probe relative to the reference marker based on the generated model, ultrasound probe position data, collected visible light image data and/or light-based depth data, and client device position/orientation information. The client device 702 may then determine a location of the target probe position in the generated model relative to the reference marker and current probe position.

The target probe position may be displayed on display 704 as an augmented reality object 712. Based on the obtained target probe position, the client device 702 may determine a location and orientation of the target probe position within the model and then generate and display the augmented reality object 712 such that it is displayed in a location on display 704 that correlates to the actual target probe position relative to the reference marker 714. The augmented reality object 712 may be body-locked to the reference marker 714, such that when a position of the reference marker 714 changes, the position of the augmented reality object 712 changes in corresponding manner. In some examples, one or more a guidance indicators, such as the illustrated arrow, may be displayed to guide the user to reposition the probe into the target probe position. Additional or alternative guidance indicators may include displayed instructions, output audio commands, or other guidance indicators. Further, once ultrasound image acquisition commences, ultrasound images 716 (e.g., obtained and displayed in real-time) may be displayed on the display 704 of the client device 702.

The depiction of the target probe position described above (e.g., as an augmented reality object positioned within a generated model of the physical environment) is an example mechanism by which the target probe position may be depicted, and other mechanisms are within the scope of this disclosure. For example, the guidance mechanisms described above (such as the augmented reality-based guidance described with respect to FIG. 7 or the virtual depictions described above with respect to FIGS. 5 and 6) may be used to provide a coarse positioning of the ultrasound probe to the target probe position. Then, once at the target probe position, the acquired ultrasound image data may be compared to stored ultrasound image data at the target scan plane acquired during a prior imaging session. If the acquired ultrasound image data does not match the stored ultrasound image data, the user may be instructed to perform a fine adjustment of the ultrasound probe position until the acquired ultrasound image data matches the stored ultrasound image data. Because some features of the imaged anatomy of the patient may change over the course of the medical procedure, the comparison of the acquired ultrasound image data and stored ultrasound image data may be restricted to anatomical regions not predicted to change, such as the tissue surrounding the ovaries rather than the ovaries themselves.

Thus, the methods and systems described herein provide for an ultrasound probe that includes position sensors and memory to allow for intelligent and reproducible guidance of the ultrasound probe. By doing so, precise and reproducible scans of the tissue in question may be performed by the operator over a period of time. Further, the image data obtained may be reconstructed into a three-dimensional volume and sent to a remote device for evaluation by a clinician. Furthermore, due to the inclusion of position information along with image data acquired, subsequent images may be aligned or projected onto previously acquired images that would provide a user with a timeline of how the follicles are maturing.

The technical effect of providing a position tracking device on an ultrasound probe and using output from the position tracking device to guide a user to position the ultrasound probe at a target position is to enable accurate image acquisition of an anatomy of interest by a non-clinically trained user in a home environment, thus reducing the burden placed on the user during medical procedures that include frequent imaging sessions.

An example system for ultrasonically scanning a tissue sample is provided. The system includes a hand-held ultrasound probe including a transducer array of transducer elements; a probe position tracking device including one or more position sensors coupled to the ultrasound probe; and a controller. The controller is configured to, during an imaging session, determine a position of the ultrasound probe relative to a target position based on position data collected by the probe position tracking device; and responsive to an indication that the ultrasound probe is at the target position, acquire image data with the transducer array.

In an example, the probe is aligned to acquire the image data in a specified target plane when the probe is at the target position, the target plane identified during a prior imaging session. In an example, the controller is configured to receive target position data specifying the target position from a remote device, the target position data identified during the prior imaging session. In another example, the controller is configured to store target position data specifying the target position in memory during the prior imaging session and obtain the target position data to determine the target position during the imaging session.

In an example, in order to determine the position of the ultrasound probe relative to the target position based on the position data, the controller is configured to determine the position of the ultrasound probe relative to the target position based on the position data and further based on a position of one or more reference markers. In an example, the controller is configured to, responsive to determining that the ultrasound probe is not at the target position, output feedback to guide a user to position the ultrasound probe at the target position. In an example, the controller is coupled to a display device, and the feedback output by the controller is configured to be displayed on the display device via a user interface. In some examples, the feedback may be displayed in the form of an augmented reality object overlaid on visible light images collected by an imaging sensor associated with the display device.

In an example, the controller is further configured to send the image data to a remote computing device. In an example, the imaging session is performed as part of a medical procedure, and the controller is further configured to perform image recognition on the image data to automatically identify a stage of the medical procedure.

An example method for an ultrasound imaging device including a hand-held ultrasound probe is provided. The method includes obtaining a target probe position that is relative to a target scan plane and one or more reference markers, the target scan plane specified by a first operator during a first imaging session; determining a current probe position of the ultrasound probe relative to the target probe position based on position data obtained from a tracking device of the ultrasound probe; and responsive to the current probe position being within a threshold range of the target probe position, obtaining image data with the ultrasound probe.

In an example, the method includes, when the current probe position is outside the threshold range of the target probe position, outputting feedback to guide a second operator to move the ultrasound probe to the target probe position, and obtaining image data with the ultrasound probe may include obtaining image data with the ultrasound probe during a second imaging session, the first imaging session occurring prior to the second imaging session.

In an example, obtaining image data with the ultrasound probe responsive to the current probe position being within the threshold range of the target probe position includes determining that the current probe position is within the threshold range of the target probe position; responsive to the determining, outputting a notification to inform the second operator that the current probe position is within the threshold range of the target probe position; and obtaining the image data responsive to a user input received from the second operator.

In an example, obtaining image data with the ultrasound probe responsive to the current probe position being within the threshold range of the target probe position includes determining that the current probe position is within the threshold range of the target probe position; and responsive to the determining, automatically obtaining the image data. In an example, obtaining image data with the ultrasound probe comprises obtaining volumetric image data with the ultrasound probe.

Another example of a method for an ultrasound imaging device including a hand-held ultrasound probe is provided. The method includes, during a first imaging session: receiving an indication of a first target anatomy to be imaged; obtaining a first target probe position corresponding to a position of the ultrasound probe at which the first target anatomy is imageable in a first target scan plane; determining a current probe position of the ultrasound probe; responsive to the current probe position being outside a threshold range of the first target probe position, outputting instructions to guide a user to adjust the current position of the ultrasound probe; and responsive to the current probe position being within the threshold range of the first target probe position, acquiring volumetric image data of the first target anatomy at the first target scan plane.

In an example, the method further includes after acquiring volumetric image data of the first target anatomy at the first target scan plane, receiving an indication of a second target anatomy to be imaged; obtaining a second target probe position corresponding to a position of the ultrasound probe at which the second target anatomy is imageable in a second target scan plane; determining the current probe position of the ultrasound probe; responsive to the current probe position being outside a threshold range of the second target probe position, outputting instructions to guide a user to adjust the current position of the ultrasound probe; and responsive to the current probe position being within the threshold range of the second target probe position, acquiring volumetric image data of the second target anatomy at the second target scan plane. In an example, the first target anatomy comprises a first ovary of a patient and the second target anatomy comprises a second ovary of the patient.

In an example, the method further includes, during a reference imaging session that occurs prior to the first imaging session, identifying the first target probe position based on user input received from a second user and storing the first target probe position in memory of the ultrasound imaging device. In an example, determining the current probe position comprises determining the current probe position based on output from a position tracking device of the ultrasound probe, and wherein the current probe position and target probe position are each relative to a position of a reference marker. In an example, outputting instructions to guide the user to adjust the current position of the ultrasound probe comprises outputting an augmented reality user interface for display on a display device, the augmented reality user interface comprising one or more real-time visible light images of the user overlaid with an augmented reality object corresponding to the target probe position.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for ultrasound imaging of a patient, comprising:
during an initial imaging session,
scanning the patient to acquire initial ultrasound image data;

identifying, in the acquired initial ultrasound image data, a target scan plane including an anatomical feature within the patient; and storing at least a subset of the acquired initial ultrasound image data as a reference image acquired at the target scan plane; and during a subsequent imaging session, instructing the patient to move an ultrasound probe to acquire subsequent ultrasound image data;

automatically identifying, via a first computing device using image recognition trained via machine learning, the target scan plane in the subsequent ultrasound image data acquired by the patient during the subsequent imaging session;

storing, on the first computing device, at least a subset of the subsequent ultrasound image data acquired during the subsequent imaging session or additional ultrasound image data acquired by the patient during the subsequent imaging session after identifying the target scan plane as a subsequent image acquired at the target scan plane; and sending the subsequent image to a second computing device configured to automatically determine changes to the anatomical feature in the target scan plane by comparing the reference image to the subsequent image.

2. The method of claim 1, further comprising performing the subsequent imaging session at a same location as the initial imaging session.

3. The method of claim 1, further comprising performing the subsequent imaging session at a different location than the initial imaging session.

4. The method of claim 3, wherein the initial imaging session is performed at any of a clinic or a hospital, and wherein the subsequent imaging session is performed at a home of the patient.

5. The method of claim 1, wherein the anatomical feature comprises a follicle, and wherein the determined changes to the anatomical feature include one or more of a change in position of the follicle and a change in size of the follicle.

6. The method of claim 5, further comprising aligning and projecting the anatomical feature in the subsequent image onto the reference image to provide a timeline of how the follicle is maturing.

7. The method of claim 1, further comprising performing image recognition on the subsequent image of the target scan plane to automatically determine the changes to the anatomical feature in the target scan plane.

8. The method of claim 7, further comprising automatically identifying, using the image recognition on the subsequent image, a stage of a medical procedure.

9. The method of claim 1, wherein identifying the target scan plane including the anatomical feature within the patient during the initial imaging session comprises receiving user input identifying the target scan plane, and wherein, during the subsequent imaging session, prior to identifying the target scan plane, two-dimensional ultrasound image data is acquired and, once the target scan plane is identified, volumetric ultrasound data is acquired.

10. A system for ultrasound imaging, comprising:
a hand-held ultrasound probe including a transducer array of transducer elements; and
a controller coupled to the hand-held ultrasound probe and configured to:
access information of a target scan plane identified during a prior imaging session, the target scan plane including an anatomical feature in a patient;

instruct, during an imaging session, a patient to move the hand-held ultrasound probe to acquire a plurality of ultrasound images;

instruct, during the imaging session, the patient to move the hand-held ultrasound probe to acquire a plurality of ultrasound images corresponding to a plurality of scan planes;

automatically identify, via machine learning, a scan plane of the plurality of scan planes corresponding to the target scan plane;

store an ultrasound image, of the plurality of ultrasound images, acquired at the target scan plane; and send the ultrasound image to a remote computing device configured to automatically determine changes to the anatomical feature depicted in the ultrasound image of the target scan plane relative to at least one reference image acquired at the target scan plane during the prior imaging session.

11. The system of claim 10, wherein the remote computing device is further configured to detect the anatomical feature in the ultrasound image, wherein the anatomical feature comprises a follicle, and wherein the determined changes to the anatomical feature include one or more of a change in position of the follicle and a change in size of the follicle.

12. The system of claim 11, wherein the remote computing device is further configured to align and project the anatomical feature in the ultrasound image onto the reference image to provide a timeline of how the follicle is maturing.

13. The system of claim 10, wherein the remote computing device is further configured to perform image recognition on the ultrasound image acquired at the target scan plane to automatically determine the changes to the anatomical feature in the target scan plane.

14. The system of claim 13, further comprising automatically identifying, using the image recognition on the ultrasound image, a stage of a medical procedure.

15. A system for ultrasonically scanning a patient, comprising:
a hand-held ultrasound probe including a transducer array of transducer elements; and
a controller configured to:
during an initial imaging session,
receive identification of a target scan plane including an anatomical feature within the patient; and
store a reference image acquired at the target scan plane including the anatomical feature; and
during a subsequent imaging session,
instruct the patient to move the hand-held ultrasound probe to acquire a plurality of ultrasound images corresponding to a plurality of scan planes;
automatically identify, using image recognition trained via machine learning, a scan plane of the plurality of scan planes corresponding to the target scan plane;
store an ultrasound image, of the plurality of ultrasound images, acquired at the target scan plane; and
send the ultrasound image acquired at the target scan plane to a remote computing device configured to automatically determine changes to the anatomical feature in the target scan plane by comparing the ultrasound image to the reference image.

16. The system of claim 15, wherein the subsequent imaging session is performed at a same location as the initial imaging session.

17. The system of claim 15, wherein the initial imaging session is performed at any of a clinic or a hospital, and wherein the subsequent imaging session is performed at a home of the patient.

18. The system of claim 15, wherein the anatomical feature comprises a follicle, and wherein the determined changes to the anatomical feature include one or more of a change in position of the follicle and a change in size of the follicle.

19. The system of claim 18, wherein the remote computing device is further configured to align and project the anatomical feature in the ultrasound image onto the reference image to provide a timeline of how the follicle is maturing.

20. The system of claim 15, wherein the controller is further configured to receive the identification of the target scan plane including the anatomical feature within the patient manually from user input or automatically from image recognition.

* * * * *